US00PP26119P3

(12) United States Plant Patent
Byrne et al.

(10) Patent No.: US PP26,119 P3
(45) Date of Patent: Nov. 24, 2015

(54) PEACH TREE NAMED 'TEXFIRST'

(50) Latin Name: *Prunus persica*
Varietal Denomination: TexFirst

(71) Applicant: TEXAS A&M UNIVERSITY, College Station, TX (US)

(72) Inventors: David H. Byrne, Bryan, TX (US); Natalie Anderson, Calvert, TX (US)

(73) Assignee: THE TEXAS A&M UNIVERSITY, College Station, TX (US)

( * ) Notice: Subject to any disclaimer, the term of this patent is extended or adjusted under 35 U.S.C. 154(b) by 0 days.

(21) Appl. No.: 13/986,482

(22) Filed: May 7, 2013

(65) Prior Publication Data

US 2014/0338077 P1 Nov. 13, 2014

(51) Int. Cl.
*A01H 5/08* (2006.01)

(52) U.S. Cl.
USPC ..... Plt./197
CPC ..... *A01H 5/0868* (2013.01)

(58) Field of Classification Search
USPC ..... Plt./197
See application file for complete search history.

(56) References Cited

PUBLICATIONS

HortScience 47(12): 1803-1804, 2012.*
Byrne, D.H. and N. Anderson, TexFirst, an Early-ripening, Low-chill Peach for the Subtropics, HortScience, 47(12):1803-1804, 2012.

* cited by examiner

*Primary Examiner* — Keith O. Robinson
(74) *Attorney, Agent, or Firm* — Jondle & Associates, P.C.

(57) ABSTRACT

Disclosed is a new and distinct variety of *Prunus persica* named 'TexFirst'. This new variety, which requires 150 to 200 chilling units of dormancy, is considered to be a peach tree of early season maturity, which produces yellow fleshed fruit that are very firm, attractively colored, and suitable for both local and long-distance shipping.

4 Drawing Sheets

Genus and species: *Prunus persica.*
Variety denomination: 'TexFirst'.

BACKGROUND OF THE NEW PLANT

This invention relates to a new and distinct peach tree variety of *Prunus persica* named 'TexFirst'. 'TexFirst', which requires approximately 150 to 200 chilling units of dormancy, produces an exceptionally high quality, firm clingstone peach that matures early in the season.

ORIGIN OF THE VARIETY

Peach tree 'TexFirst' is the result of an ongoing Stone Fruit Breeding Program of Texas A & M University, College Station, Brazos County, Tex. To this end, both controlled and hybrid crosses are made each year in order to produce seedling populations from which improved progenies are evaluated and selected.

The seedling 'TexFirst' originated at the Texas A & M University Horticultural Farm in College Station, Tex. in 1998, and was chosen as 'TX1A95' from a population of seedlings that resulted from seed from an open pollinated seed lot from the Thai Tiger low chill peach 'TXW1193-1', (Byrne and Boonprakob, HortScience 43:2226-2227, 2008) an unpatented peach selection of unknown parentage released for use by the Royal Project of Thailand for the development of the peach industry of the low chill tropical zones in northern Thailand. The pollen parent of 'TexFirst' is not known. The seedling denominated as 'TX1A95' was selected for its early maturity, good productivity, yellow ground color, round shape, high red overcolor, and excellent firmness. Resulting seed from this cross were planted in 1996 at the Texas A & M University Horticultural Farm in College Station, Tex. 'TexFirst' was marked for subsequent observation and noted as having exceptional characteristics. Two-year and older trees of the variety were subsequently evaluated during the 2000 through 2010 fruit growing seasons in both California (Clovis) and Texas (Floresville and College Station).

ASEXUAL REPRODUCTION OF THE VARIETY

'TexFirst' was bud grafted onto virus-free Nemaguard ("The Brooks and Olmo Register of Fruit and Nut Varieties," 3rd Ed., American Society of Horticultural Science Press, Alexandria, Va., 1997) peach rootstock in June 1998 at the nursery site in Oakdale, Calif. The variety was subsequently planted at the experimental orchard in the central portion of the San Joaquin Valley, near Fowler, Fresno County, Calif. and in two sites in Texas (College Station and Floresville). Fruit from the resulting propagation has been evaluated during the period from 2000 to 2010 fruit seasons. This evaluation clearly demonstrated that the re-propagated trees were true to the characteristics of the original seedling in all observable aspects. The present invention has been found to retain its distinctive characteristics through successive asexual propagations via budding.

Plant Breeder's Rights for this variety have not been applied for. 'TexFirst' has not been made publicly available or sold anywhere in the world more than one year prior to the filing date of this application.

SUMMARY OF THE INVENTION

The new peach tree variety 'TexFirst' is characterized as to novelty and is otherwise noteworthy by producing fruit that ripens in the early season; is considered high quality; and which is firm and has an attractive coloration. In this regard, the present variety of peach tree bears fruit that are ripe for commercial harvesting and shipment in mid May, when the fruit is grown in the San Joaquin Valley of Central California and the last week of April when grown in the medium chill zone of Texas. 'TexFirst' ripens 7-8 days earlier than the 'Flordaking' Peach, a non-patented variety (Anderson et al., HortScience, 14:81-82, 1979). The new variety exhibits the potential to be commercialized in low and medium chill regions.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from 7-year old trees.

FIG. 1 shows 'TexFirst' ('TX1A95') fruit (left) as compared to fruit from 'Flordaking' (unpatented; center) and 'TexKing' (U.S. Plant Pat. No. 14,627; right). These fruit were grown in Floresville, Tex. and harvested on 30 April, 6 May and 22 May of 2007 respectively.

DESCRIPTION OF THE NEW VARIETY

Figure 1:
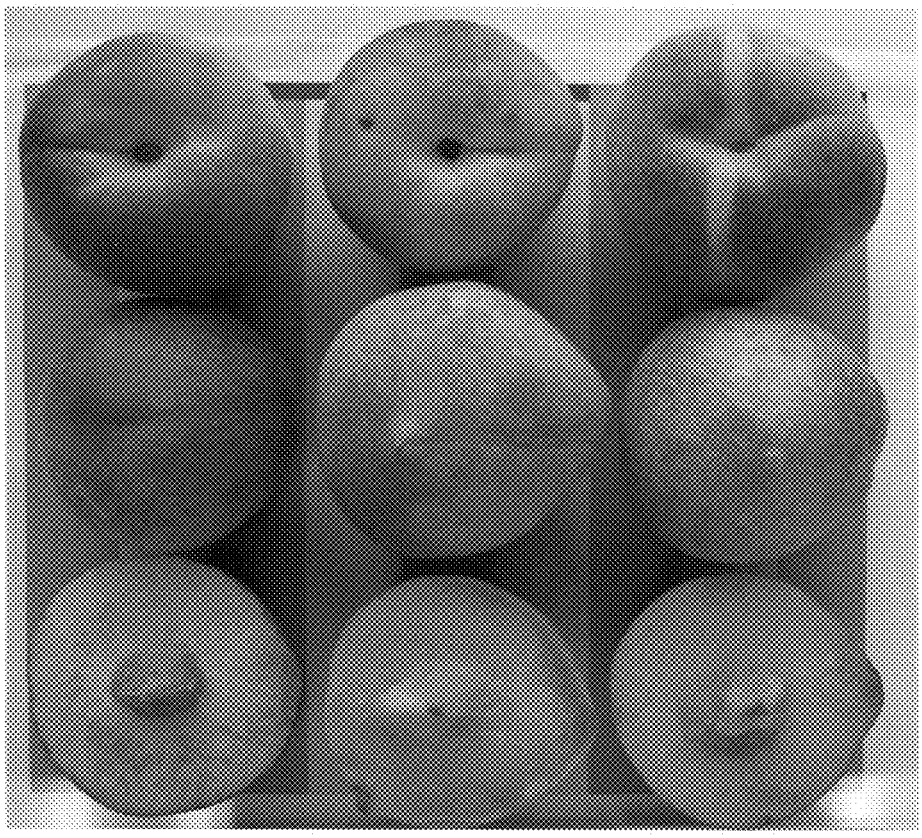
Figure 2:
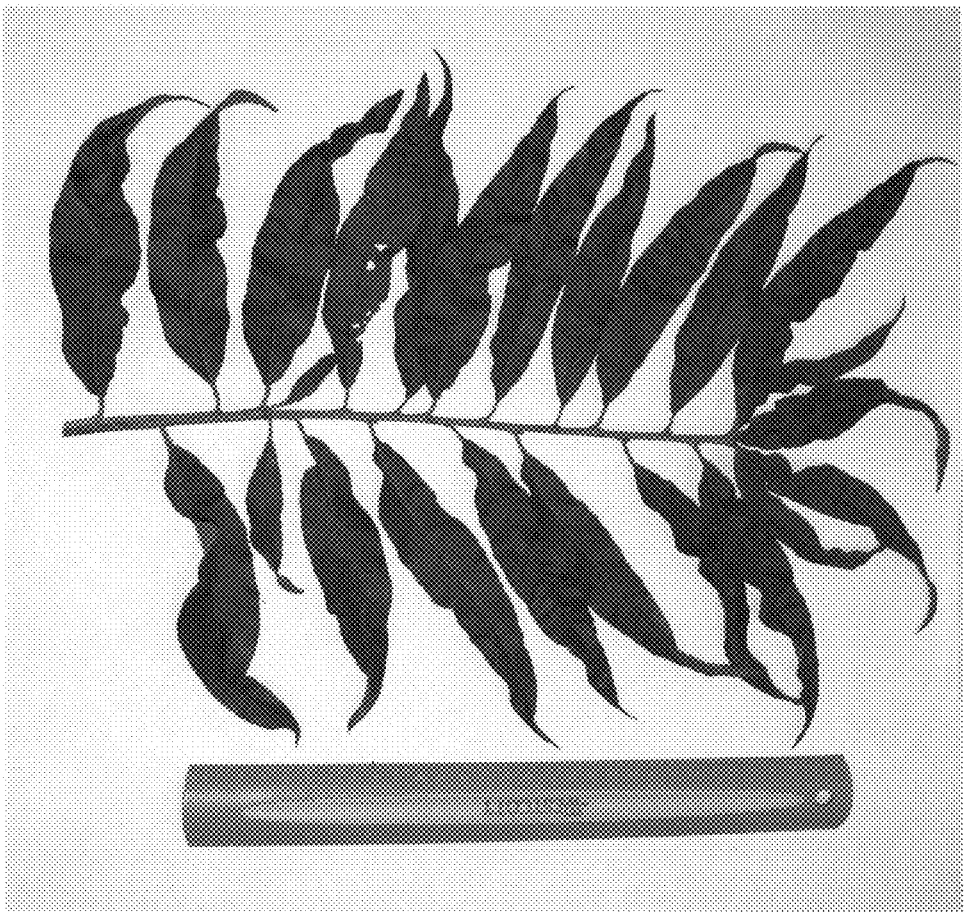
FIG. 2 shows a shoot of 'TexFirst' showing leaves and young stem.
Figure 3:
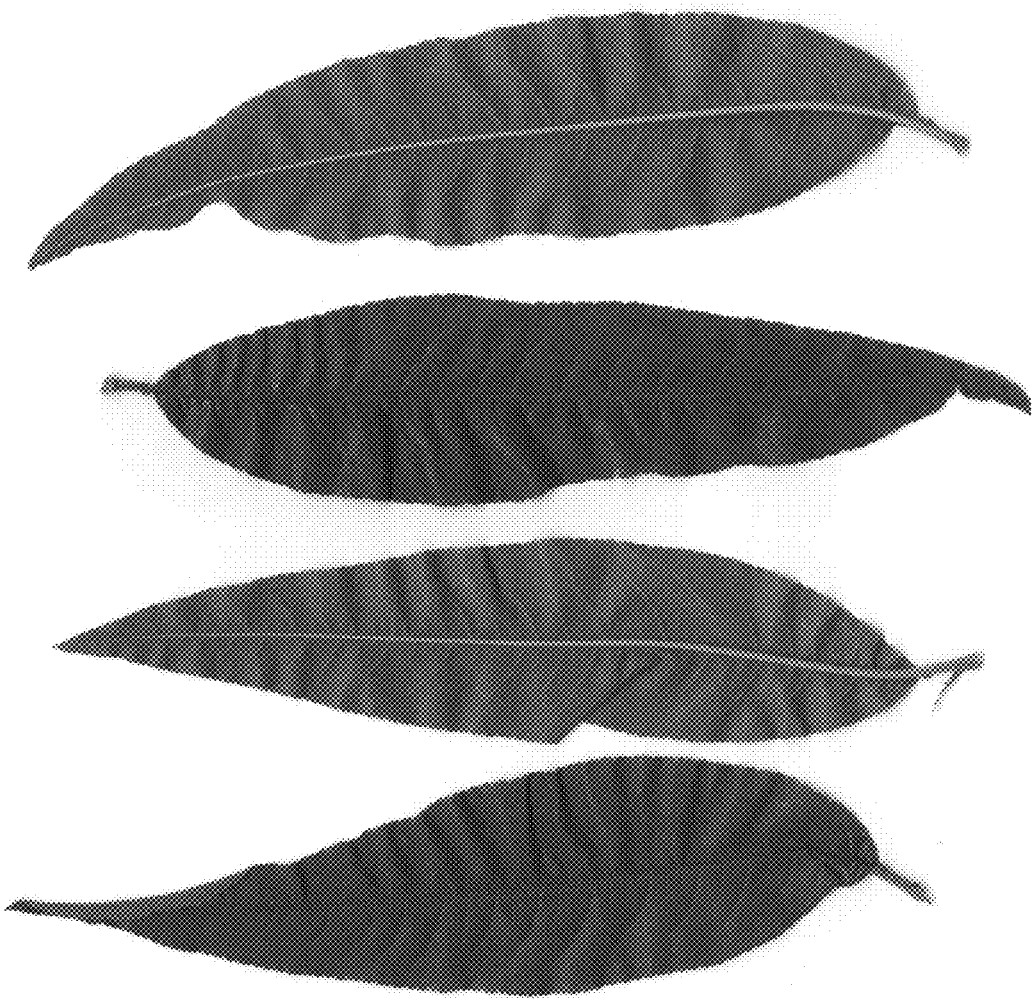
FIG. 3 shows the abaxial and adaxial surfaces of the leaves of 'TexFirst'.
Figure 4:
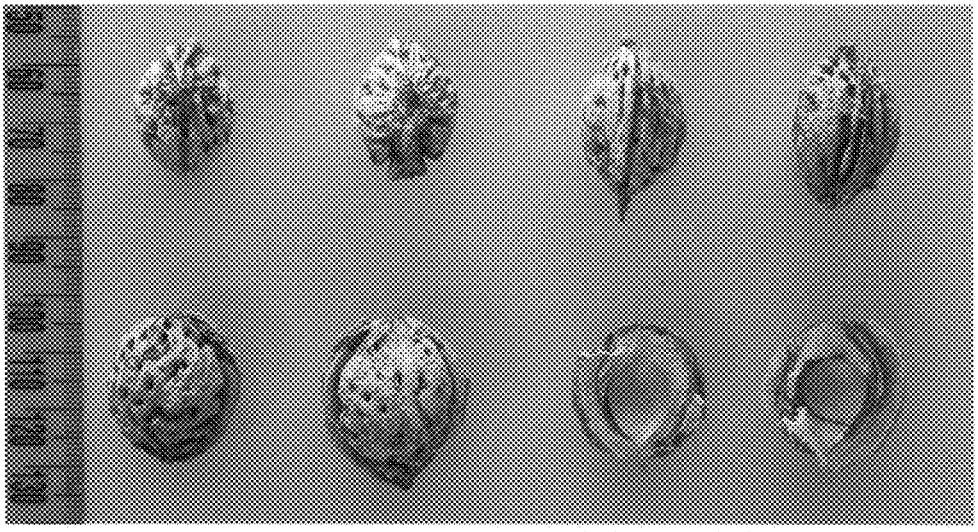
FIG. 4 shows various views of the endocarp of the cultivar 'TexFirst'. The scale is in millimeters.

The following detailed descriptions set forth the distinctive characteristics of 'TexFirst'. The data which define these characteristics is based on observations taken at experimental orchards in Fowler, Calif. from 2000 to 2010. Color designations, color descriptions, and other phenotypical descriptions may deviate from the stated values and descriptions depending upon variation in environmental, seasonal, climatic and cultural conditions. 'TexFirst' has not been observed under all possible environmental conditions. The botanical description of 'TexFirst' was taken from 7-year old trees. Color terminology follows The Royal Horticultural Society Colour Chart, London (R.H.S.) (Published 2001). Colors are approximate as color depends on horticultural practices such as light level and fertilization rate, among others.

DETAILED BOTANICAL DESCRIPTION

Classification:

*Family*.—Rosaceae.

*Botanical*.—*Prunus persica*.

*Common name*.—Peach.

*Variety name*.—'TexFirst'.

Tree:

*Size*.—Generally average to above average as compared to other common peach cultivars ripening in the early season of maturity

*Height*.—8.5 feet (2.58 m) at the end of the 2008 growing season.

*Width*.—6.2 feet width (1.80 m) at the end of the 2008 growing season.

*Vigor*.—High.

*Density*.—Medium to high.

*Productivity*.—Productive.

*Shape*.—The 'TexFirst' peach has been trained in central lead configuration but exhibits a generally spreading growth habit typical of common low and medium chill commercial varieties of peach such as 'TropicPrince' (U.S. Plant Pat. No. 12,965), 'TropicBeauty' (Rouse and Sherman, HortScience 24:165-166, 1989) and 'TexKing' (Byrne and Bacon, HortScience 39:442-443, 2004).

*Current season growth*.—The current season growth for the new variety was approximately 3.0 to 3.3 feet (0.91-1.12 m).

*Regularity of bearing*.—Regular, and considered hardy under the typical conditions found in the central San Joaquin Valley, Calif. and in south central Texas (Floresville and College Station).

Trunk:

*Size*.—Approximately 3.4 inches (8.63 cm) in diameter and 11.4 inches (29.0 cm) in circumference when measured at a distance of approximately 12 inches (30.5 cm) above the soil level, at the end of the 2008 growing season on a five-year old tree.

*Bark texture*.—Considered moderately rough with numerous folds of papery scarf-like skin being present.

*Bark coloration*.—Variable, colors (R.H.S. colors) present are 166A, 174A, 175A, 175B, and 175C of the Grey Orange group, 201A and 201B of the Grey group, and 201C and 201D of the Brown group.

Branches:

*Length*.—Considered medium for the variety. Depending on soil, fertility and climate, a minimum growth of 1 meter is expected, but with high fertility can reach 2.5 meters or greater.

*Width*.—Average (about 2.5 cm in diameter as measured 10 cm from the trunk on a five-year old tree) as compared to other varieties.

*Surface texture*.—Appearing furrowed on wood that is several years old.

*Lenticels*.—Numerous flat, oval lenticels present. The lenticels range in size from approximately 4.0 to 6.0 mm in width and were approximately 1 mm in height.

*Current season shoots*.—Surface texture — Substantially glabrous.

*Internode length*.—Approximately 2.0 to 2.5 cm as measured in the middle of a current season stem.

*Color of mature branches*.—The predominant colors (R.H.S. colors) are 165A, 165B and 177B of the Grey Orange group, 199B and 199C of the Grey Brown group, and 200D of the Brown group.

*Current season shoots*.—Color (R.H.S. colors) — Light green (143B and 143C of Green group and 144A, 144B and 144C of the Yellow Green Group) with some reddish-brown coloration appearing on exposed surface of the shoots (165A, 165B, and 167A of the Grey Orange group). The color of new shoot tips is considered a bright and shiny green (mainly RHS Green Group 141A-C and 144A).

Leaves:

*Size*.—Considered moderately large for the species. Leaf measurements have been taken from vigorous upright current season growth approximately at mid-shoot.

*Leaf length*.—Approximately 162 to 180 mm.

*Leaf width*.—Approximately 37 to 40 mm.

*Leaf thickness*.—Approximately 1 mm.

*Leaf form*.—Lanceolate.

*Leaf tip form*.—Acuminate.

*Leaf upper surface color*.—Green varying among 146A and 146C of the Yellow Green group.

*Leaf lower surface color*.—Green varying among 146B, 146C and 146D of the Yellow Green group.

*Leaf mid-vein color*.—Light yellow green (N144C-D and 144B-D Yellow Green Group).

*Leaf margins*.—Form: Considered crenate. Uniformity: Considered generally uniform.

*Leaf petioles*.—Size: Considered medium long. Length: Approximately 12 to 14 mm. Width: Approximately 1 to 2 mm. Color: Pale green (RHS Yellow Green Group 144A-C).

*Leaf glands*.—Size: Approximately 1 mm in height and 1 to 1.5 mm in width. Number: Generally 2-4 per leaf. Type: Reniform. Color: Greenish brown (199A RHS Grey Brown Group).

*Leaf stipules*.—Size: Small for the variety. Length: Approximately 2 to 3 mm. Width: Generally approximately 1 to 2 mm. Form: Lanceolate. Color: Green (RHS Yellow-Green 144B-C) with reddish brown tips (RHS Greyed-Orange Group 166A-B and 175A-B) when young. The stipules are considered to be early deciduous.

*Ratio of wood (leaf) buds to flowering buds*.—1 to 2 flower buds per vegetative bud.

Flowers:

*Floral buds*.—General: The floral buds are considered to be medium to medium large in size, conic in form, and slightly appressed relative to the bearing shoot. Color: The bud scales are gray-brown, (approximately RHS Greyed Orange Group 165A and 166A and Grey Brown Group N199B). The buds are considered hardy under typical central San Joaquin Valley, Calif. climatic conditions. Length: Approximately 5 to 7 mm. Density: Dense.

*Blooming type*.—Considered quite early in relation to other peach cultivars commonly growing in the central San Joaquin Valley. Date of full bloom was between February 5$^{th}$ and February 16$^{th}$ during the period between 2005 and 2010. It blooms at the same time as the low chill varieties "TropicPrince' and 'TropicBeauty'.

*Flower type*.—Showy.

*Flower size*.—Flower diameter at full bloom is approximately 28 to 32 mm.

*Bloom quantity*.—Considered abundant.

*Flower bud frequency*.—Normally 1 to 2 per node.

*Petal size*.—General: Considered medium to medium large for the species. Width: Approximately 9 to 10 mm. Length: Approximately 15 mm.

*Petal form*.—Broadly ovate.

*Petal count*.—Nearly always 5.

*Petal color*.—Light pink when young (RHS White Group N155B-C), becoming darker near the petal claw.

*Petal claw*.—Form: The claw is considered truncate in shape and has a medium size when compared to other varieties. Length: Approximately 1 to 1.5 mm. Width: Approximately 1 to 1.5 mm.

*Petal margins*.—Generally considered variable, from nearly smooth to slightly undulate.

*Petal apex*.—Generally the petal apices appear slightly domed.

*Flower pedicel*.—Length: Considered short, and having an average length of approximately 2 to 2.5 mm. Width: Considered average, approximately 0.5 to 1 mm. Color: A light green (RHS Yellow-Green Group N144A-D).

*Floral nectaries*.—Color: Dull orange to orange-gold (RHS Greyed-Orange Group 170B).

*Calyx*.—Surface Texture: Generally glabrous. Color: A brownish red (approximately RHS Greyed-Red Group 178A-B).

*Sepals*.—Surface Texture: The surface has a short, fine, wooly and a gray-colored texture. Shape: Ovate. Color: A dull red (approximately RHS Greyed-Orange Group 176A-B).

*Anthers*.—General: Average in size for the species. Color: Golden yellow (approximately RHS Yellow Orange Group 17A-B).

*Pollen production*.—Pollen is abundant, and is a yellow color (approximately RHS Yellow Orange 16A).

*Filaments*.—Size: Variable in length, approximately 12 to 13 mm, with the filaments slightly shorter than the pistil. Color: White with pink tinge (approximately RHS White Group 155A-D) and darkening with advanced maturity.

*Pistil*.—General: Average in size, but slightly longer, relative to the general anther height, overall. Length: Approximately 15 to 17 mm, including the ovary. Color: Considered a very light yellow when young (approximately RHS Yellow Group 9C-D and 10C-D), and becoming slightly darker with advancing senescence.

*Surface texture*.—The variety has a long, silver white pubescent pistil (approximately RHS White Group 155A-D).

Fruit:

*Maturity when described*.—The present variety of fruit is described, as it would be found in its firm ripe condition at full commercial maturity. Under the ecological conditions prevailing in the San Joaquin Valley of Central California: Average ripe date was May 17$^{th}$ with or slightly before the low chill peach 'TropicPrince' and 8 days before the medium chill peach 'Flordaking'.

*Size*.—General — Medium to medium large for the season and considered uniform. Average Cheek Diameter: Approximately 58 to 63 mm. Average Suture Diameter: Approximately 53 to 61 mm. Average Axial Diameter: Approximately 62 to 67 mm.

*Fruit form*.—Generally quite ovate in its lateral aspect. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Color: The suture normally is the same color as the underlying blush (RHS Orange-Red Group 34A and N34A).

*Ventral surface*.—Form — Considered uniform.

*Stem cavity*.—Size: Considered moderately shallow for the species. Width: Approximately 12 to 18 mm.

Length: Approximately 16 to 19 mm. Depth: Approximately 9 to 11 mm. Form: Considered variable from round to flat.

*Fruit base*.—Generally considered truncate in form, and uniform.

*Fruit apex*.—Generally considered depressed and usually recessed below the height of the apical shoulders.

*Fruit stem*.—Length: Considered medium in length, approximately 8 to 9 mm. Thickness: Approximately 2 to 4 mm. Color: Generally a light green with brown (RHS Yellow-Green Group 144A-C, Greyed-Orange Group 165A and Greyed-Orange Group 166A).

*Fruit skin*.—Thickness: Generally considered medium or average in thickness. Surface Texture: The variety has very light, short pubescence. Skin Acidity: Considered neutral. Tenacious to Flesh: Yes at commercial maturity. Tendency to Crack: Not observed. Skin Color: Variable, with approximately 40-65% of the fruit surface covered with an attractive orange red blush that ranges from an orange red (RHS Orange Red 34A to N34A) to red (RHS Red 42A). Down: Light and short. Blush Color: The blush color is generally more prevailing apically. This red blush ranges from an orange red (RHS Orange Red 34A to N34A) to red (RHS Red 42A) with many degrees of shading and blending occurring between these colorations. The type of blush coloration would be categorized as a striped, chimeric or tigered covering. Skin Ground Color: This is generally present in variable percentages covering approximately 35-60% of the fruit's surface. The skin ground is a yellow green color (approximately RHS Green Yellow Group 1B-C).

*Flesh color*.—Generally considered variable from a yellow to orange (RHS Yellow Group 4A-C and 9D and Orange Group 24B-C).

*Flesh fibers*.—Present, numerous and lightly colored. These fibers are present throughout the flesh.

*Stone cavity color*.—Generally considered variable from a yellow to yellow green color (RHS Green Yellow Group 1A-C).

*Flesh texture*.—Generally, the flesh is considered firm and fine at commercial maturity.

*Ripening*.—Generally the fruit ripens evenly.

*Flavor*.—Considered very sweet and a rich, with slightly acidic flavor.

*Aroma*.—Pleasant and reasonably abundant.

*Eating*.—Generally considered very good to excellent, particularly for an early ripening variety.

Stone:

*Attachment*.—Clingstone at commercial maturity.

*Stone size*.—Generally considered medium to medium-large relative to the ratio of stone to fruit size. Length: Approximately 27.5 to 30 mm. Width: Approximately 23 to 25 mm. Thickness: Approximately 17 mm.

*Fibers*.—Generally a few medium length fibers are attached along the entire surface of the stone.

*Stone form*.—Generally the stone is considered oblate to round.

*Stone base*.—The stone is medium to wide.

*Base angle*.—The base angle of the stone is variable, but most frequently is considered slightly oblique to the stone axis.

*Hilum*.—Generally considered medium in size, and rather poorly defined as is common in very early ripening varieties. The hilum is approximately 4 to 5 mm long and 2 to 4 mm wide. Form: Considered oval.

*Apex shape*.—The stone apex is wide.

*Stone shape*.—Considered variable. The stone normally ovid to elongated.

*Stone surface*.—Surface Texture: Minor surface markings are honeycombed with numerous single pits with a few rosettes of pits. Ridges: Numerous fine ridges are present basally, and converge towards the base of the stone.

*Ventral edge*.—Width — Considered small to medium and having a dimension of approximately 6 to 7 mm at the mid-suture.

*Dorsal edge*.—Shape — Grooved and having moderately rough edges.

*Stone color*.—The color of the dry stone is light brown (RHS Greyed-Orange Group 164B-C and Greyed-Yellow Group 161A). The color of the inside surface of the endocarp is primarily RHS Greyed Orange 164C and 164D.

*Tendency to split*.—Splitting is relatively uncommon.

*Kernel*.—The kernel fills the endocarp at harvest and measures approximately 5-6 mm in thickness, 9-11 mm in width, and 15-16 mm in length. When dried the shriveled kernels measure approximately 1-1.5 mm in thickness, 7-9 mm in width, and 12-14 mm in length. The colors of the shriveled kernels are primarily RHS Greyed Orange Group 165B and Greyed Brown Group N199C-D.

*Use*.—'TexFirst' is considered to be a peach tree of early-season maturity, which produces fruit which are very firm, attractively colored, and which are useful for both local and long distance shipping.

*Keeping quality*.—Good.

*Resistance to insects and disease*.—No particular susceptibilities were noted.

*Shipping quality*.—Average.

COMPARISON WITH PARENTAL AND COMMERCIAL VARIETIES

'TexFirst' differs from parental peach 'TXW1193-1' in that 'TXW1193-1' blooms 1-6 days before 'TexFirst' and ripens 15-39 days after 'TexFirst' depending on the location and year.

'TexFirst' can be compared to commercial varieties 'Flordaking' (unpatented) and 'TexKing' (U.S. Plant Pat. No. 14,627). Table 1 shows a comparison of fruiting characteristics of 'TexFirst' compared to 'Flordaking' and 'TexKing' from data taken in Floresville, Tex. from 2003 to 2010. Table 2 shows a comparison of fruiting characteristics of 'TexFirst' compared to 'Flordaking' and 'TexKing' from data taken in Fowler, Calif. from 2000 to 2010. For Tables 1 and 2: full bloom indicates 60-80% of flowers are open; FDP indicates the fruit development period (number of days from full bloom to ripe); ripe date indicates the date when 20% of fruit is at the firm ripe stage; size indicates a rating of diameter in millimeters (mm) from 0 to 9, where 4 equals 51 to 57 mm, 5 equals 58 to 64 mm, 6 equals 65 to 70 mm, and 7 equals 71 to 76 mm; the data for firm, shape, tip, ground color, appearance and taste are given in terms of a rating scale from 0 to 9, where 0 to 4 equal unacceptable, 5 equals marginal, 6 equals good, 7 equals very good, and 8 to 9 equal excellent for commercial use; blush is rated on a percent basis, where 0 equals no red, 5 equals 50% of skin surface with red, and 9 equals 90% or more of the skin surface with red; the mean separation within columns by Duncan's Multiple Range test at the 5% level is shown as items with the same letter are not significantly different, whereas no letters within a column indicates no significant differences.

TABLE 1

Fruiting characteristics of 'TexFirst' compared to 'Flordaking' and 'TexKing' at Floresville, TX

| Name | Full bloom | FDP (days) | Ripe date | Size | Weight (g) | Firm | Blush |
|---|---|---|---|---|---|---|---|
| TexFirst | Jan. 29 b | 87 a | Apr. 26 c | 4.9 b | 109 b | 7.3 a | 7.2 a |
| Flordaking | Feb. 18 a | 78 b | May 03 b | 6.2 a | 137 a | 6.2 c | 3.4 c |
| Texking | Feb. 19 a | 85 a | May 14 a | 6.1 a | 140 a | 7.0 b | 5.6 b |

| Name | Shape | Tip | Ground color | Appearance | Soluble solids (Brix) | Taste |
|---|---|---|---|---|---|---|
| TexFirst | 7.9 a | 7.9 a | 7.0 a | 7.8 a | 10.0 | 6.2 |
| Flordaking | 5.7 b | 5.9 b | 6.1 b | 5.5 c | 9.3 | 5.7 |
| Texking | 6.0 b | 6.3 b | 6.5 ab | 6.4 b | 8.9 | 5.7 |

TABLE 2

Fruiting characteristics of 'TexFirst' compared to 'Flordaking' and 'TexKing' at Fowler, CA

| Name | Full bloom | FDP (days) | Ripe date | Size | Weight (g) | Firm | Blush |
|---|---|---|---|---|---|---|---|
| TexFirst | Feb. 10 b | 96 a | May 17 c | 5.8 b | 134 b | 7.5 a | 6.0 a |
| Flordaking | Feb. 26 a | 85 b | May 25 b | 7.0 a | 178 a | 6.3 b | 3.0 b |
| Texking | Feb. 25 a | 99 a | Jun. 04 a | 7.3 a | 190 a | 7.0 ab | 6.4 a |

| Name | Shape | Tip | Ground color | Appearance | Soluble solids (Brix) | Taste |
|---|---|---|---|---|---|---|
| TexFirst | 8.1a | 8.6 a | 6.9 a | 7.0 a | 10.0 | 6.4 |
| Flordaking | 7.2 b | 7.2 b | 6.1 b | 5.4 b | 10.5 | 6.0 |
| Texking | 7.1 b | 7.4 b | 6.8 ab | 6.8 a | 10.5 | 6.2 |

We claim:

1. A new and distinct variety of *Prunus persica* tree named 'TexFirst' as described and shown herein.

* * * * *